United States Patent [19]

Shinault

[11] Patent Number: 5,407,670
[45] Date of Patent: Apr. 18, 1995

[54] TOPICAL OINTMENT FOR THE TREATMENT OF EPIDERMAL TRAUMA

[76] Inventor: Wanda K. Shinault, 2237 12 O'Clock Knob Rd., Salem, Va. 24153

[21] Appl. No.: 10,356

[22] Filed: Jan. 28, 1993

[51] Int. Cl.⁶ .............................................. A61K 31/79
[52] U.S. Cl. .............................. 424/78.06; 424/78.25; 424/667; 424/672
[58] Field of Search ................ 424/78.06, 78.25, 667, 424/672; 514/29

[56] References Cited

U.S. PATENT DOCUMENTS

| | | | |
|---|---|---|---|
| 4,079,128 | 3/1978 | Lin et al. | 514/29 |
| 4,294,852 | 10/1981 | Wildenauer et al. | 514/29 |

*Primary Examiner*—Thurman K. Page
*Assistant Examiner*—P. Kulkosky
*Attorney, Agent, or Firm*—Clyde I. Coughenour

[57] ABSTRACT

A topical ointment for the treatment of epidermal traumas such as burns, wounds, rashes lesions, and decubital ulcers (bed sores). The ointment includes a mixture of polymyxin, bacitracin, neomycin, iodine and sugar. The preferred polymyxin is polymyxin B sulfate, the bacitracin is bacitracin zinc, the neomycin is neomycin sulfate, the iodine is povidone-iodine, and table sugar.

20 Claims, No Drawings

TOPICAL OINTMENT FOR THE TREATMENT OF EPIDERMAL TRAUMA

BACKGROUND OF THE INVENTION

1. Field of the Invention

A topical ointment for the treatment of epidermal trauma such as burns, rashes, lesions, wounds and decubital ulcers is disclosed. The composition includes a mixture of polymyxin, bacitracin, neomycin, iodine and a sugar.

2. Description of Prior Art

The standard treatment for epidermal trauma such as burns, rashes, lesions, wounds, and decubital ulcers is to apply MIRACLE CREAM TM, a prescription medication, or other ointment, salve or preparation to the ulcers or other trauma area. "MIRACLE CREAM TM is an ointment containing hydrocortisone, zinc oxide and neptatin. U.S. Pat. No. 4,847,084 issued 11 Jul. 1989 to Morris Mintz states: "all these products have, in my opinion, failed to live up to their claims of healing decubiti ulcers satisfactorily and have been disappointing in many instances." Preparation for curing ailments for both internal and external body parts and functions have been available for centuries. Many of the preparations are formulated for the treatment of the skin in order to prevent and cure wounds, burns, and lesions. There are many of these preparations that can be used for prevention and/or cure of lesions such as decubital ulcers, better known as bed sores or pressure sores. The preparations have many forms such as jellies, ointments, salves, gels, sprays, creams, lotions, sticks, etc.

All of the ingredients of the present invention, namely polymyxin, bacitracin, neomycin, iodine and sugar, are known as ingredients used in topical preparations. U.S. Pat. No. 2,556,376, issued 12 Jun. 1951 to P. Regna, discusses the use of the polymyxin as an antibiotic. U.S. Pat. No. 2,680,701, issued 8 Jun. 1954 to F. Cusumano, discloses that several antibiotics, including polymyxin and bacitracin, can be used in a single preparation against a wide variety of infections. U.S. Pat. No. 2,809,149, issued 8 Oct. 1957 to F. Cusumano, reviews the "value of the synergistic combinations of polymyxin B, bacitracin and neomycin" as antibiotics in topical applications and discusses a new use for the combination as a protection for both minor and major wounds. U.S. Pat. No. 5,034,421, issued 23 Jul. 1991 to R. Fuisz, teaches that "NEOSPORIN" TM, containing essentially the ingredients addressed by F. Cusumano in U.S. Pat. No. 2,809,149, could be blended with sucrose to form a mixture that could be spun and used for delayed release burn or wound dressings, U.S. Pat. No. 5,126,127, issued 30 Jun. 1992 to D. Bhagwat et al, discusses the use of iodine in the form of povidone-iodine and its use as a microbicidal solution; and U.S. Pat. No. 4,847.084, issued 11 Jul. 1989 to M. Mintz, teaches that an iodine, in the form of povidone-iodine, can be added to ointments used in the treatment of decubiti ulcers for a better, shorter, healing time. U.S. Pat. Nos. 4,401,651, issued 30 Aug. 1983 to R. Knutson and 4,671,957, issued 9 Jun. 1987 to P. Holtshousen, and 4,844,898, issued 4 Jul. 1989 to S. Komori et al, teach adding a sugar to an iodine, povidone-iodine, to improve wound healing ability with decubitus and open wounds mentioned. U.S. Pat. No. 3,116,207 issued 31 Dec. 1963 to M. Mulinos describes a fabric coating composition consisting of neomycin and bacitracin, zinc neomycin and bacitracin, zinc bacitracin and neomycin, zinc bacitracin and zinc neomycin, copper neomycin and copper bacitracin, copper neomycin and bacitracin, and neomycin and copper bacitracin; these compositions are used for fabric coatings to prevent perspiration odor. None of the above references teach the combination of polymyxin, bacitracin, neomycin, iodine, and sugar for the treatment of epidermal trauma such as burns, wounds, rashes, lesions and decubital ulcers.

SUMMARY OF THE INVENTION

It is an object of the present invention, to provide an ointment and method for the treatment of epidermal trauma such as burns, wounds, rashes (such as those caused by diapers, irritations, and yeast infections), lesions, and decubital ulcers (bed sores).

These and other objects of the invention are accomplished by an ointment containing polymyxin, bacitracin, neomycin, iodine and sugar. The ointment can be formed by mixing the active ingredients with a topical cream base which is composed of a mixture of hydrocarbons and polyol moisturizing components. The hydrocarbon component may be selected from any of the hydrocarbon oils and hydrocarbon bases that are well known in the pharmaceutical art. Suitable hydrocarbon oils are mineral oil or liquid petrolatum, while suitable hydrocarbon bases are white petrolatum or white ointment (petrolatum with 5 percent beeswax).

DETAILED DESCRIPTION OF THE PREFERRED EMBODIMENT

The preferred embodiment of this ointment is made by mixing together 250 to 750 mg of sugar with 5 to 15 mg of iodine and 1 to 10 mg of neomycin and 1,000 to 10,000 units of polymyxin and 50 to 500 units of bacitracin. The preferred neomycin is neomycin sulfate and polymyxin is polymyxin B sulfate and bacitracin is bacitracin zinc and iodine is providone-iodine (polyvinylpyrrolidone iodine).

As a convenient example an ointment, a paste like mixture hereinafter referred to in the examples as the ointment of the present invention, was prepared by mixing or blending together BETADINE TM and NEOSPORIN TM and sugar. The ratio of the mixture prepared was essentially one (1) gram of BETADINE TM to four (4) grams of NEOSPORIN TM to five (5) grams of sugar. The resulting mixture contained essentially 5 grams of sugar, 20,000 units of polymyxin B sulfate, 1,600 units of bacitracin zinc, 20 mg of neomycin sulfate and 100 mg of iodine. The remaining ingredients were essentially 900 mg of polyvinylpyrrolidone, and about 3.94 grams of white petrolatum. The NEOSPORIN TM used included as active ingredients in each gram essentially 5,000 units of polymyxin B Sulfate, 400 units of bacitracin zinc and 5 mg of neomycin sulfate in a topical cream base (white petrolatum). The BETADINE TM used included in each gram essentially 100 mg of iodine and 900 mg of providone (polyvinylpyrrolidone iodine). The sugar used was common table sugar purchased from the grocery store.

The actual amount of the preparation that must be applied and the frequency of application depend on the specific circumstances. One application a day has been found to be sufficient for an immobile patient, while several applications may be necessary for a patient who is active or needs treatment in an area that is subject to irritation and abrasion. For best results, the affected area should be kept coated by the ointment of the present invention.

EXAMPLE I

A male patient had two pressure sores on the skin between the forefinger and ring finger of the right hand. The hand was suffering from paralysis and was contracted in a clenched fist. The sores were essentially 1½ cm. and 2 cm. in diameter and were deep enough to expose the bone and tendons of the fingers. Because of the paralysis and sore location there was poor air circulation and little or no movement of the fingers. The affected area was cleaned with hydrogen peroxide. MIRACLE CREAM TM was applied to the sores for 14 days with no noticeable improvement. NEOSPORIN TM was then applied to the sores for 7 days with no noticeable improvement. After the failure of these products to improve the condition of the patient, the ointment of the present invention was applied. The mixture was applied once each day. After seven days the smaller sore was healed. After ten days the larger sore was healed. The area of skin turned somewhat whiter than the surrounding skin and exhibited a slight hardening.

Example II

During a three month period of a patient's convalescence, fifteen small shallow sores of approximately ¼ to ½ cm appeared on the buttocks. As the sores first appeared NEOSPORIN TM was applied. After several days, no noticeable improvement was observed. Duoderm TM Patches were then applied to the sores over a period of time in excess of 60 days with no noticeable improvement. Duoderm TM Patches are not known to have any active ingredients. After the failure of these products to improve the conditions of the patient, the ointment of the present invention was applied. The sores were treated with the ointment once a day. Within 24 to 48 hours of the first treatment, each of the sores was healed. In addition to these sores, a sore appeared on each foot at the ankle bone. Each of the ankle bone sores was healed with two applications of the present ointment.

Example III

An active female patient had seven bedsores on the buttocks. The five smallest sores were about 1 cm to 1½ cm each in diameter and of a shallow depth. The remaining two sores were 2 cm to 2½ cm in length, 1¼ to 1½ cm in width, and ½ cm deep. The affected area was cleaned with hydrogen peroxide. The ointment of the present invention was then applied once each day. After two days the five smallest sores were healed. The remaining two large sores were in a position wherein they were abraded and irritated each time the patient used the bed pan. Because of the size and location of the sores, healing was not complete for 14 days. After healing, the surface exhibited a slight hardening and whitening.

Example IV

A 14 month old infant broke out with what appeared to be a "diaper rash." The affected area was treated with DESITIN TM ointment, vaseline, and corn starch over a period of two to three months without any improvement. DESITIN TM Ointment contains zinc oxide and Cod liver oil. Because the symptoms persisted and the sores began to break open, the infant was taken to a physician. The physician diagnosed the problem as being a "yeast infection" and prescribed Zinc Ointment. The condition cleared up after treatment with Zinc Ointment but returned after 24 to 36 hours of stopping the treatment. After repeated treatments with Zinc Ointment failed to cure the condition, the ointment of the present invention was applied. In 24 hours the condition was noticeably improved and after 3 days the affected area was completely clear of rash. The rash did not reappear after treatment with the ointment of the present invention was stopped.

Example V

A patient's finger was burned and a blister of about ¼ inch diameter formed. The ointment of the present invention was applied. About 12 hours later the skin of the blister was removed and a second application of the ointment was made. After 24 hours the skin was red but not sensitive to the touch.

Example VI

The top portion of a patient's hand, an area of about 1 inch square, was burned and turned a white color from contact with a hot surface. The area was promptly treated with the ointment of present invention and bandaged. After 12 hours the bandage was removed. There were no visible blisters and the surface was not sensitive to the touch.

Example VII

Both of a patient's ankles, areas of about 1 inch in length by ¼ inch in width, were blistered and then rubbed raw by frictional contact with high top shoes. The affected area was treated with the ointment of the present invention. Within 24 hours the area was healed to the point that the skin was no longer raw or sensitive to the touch.

It is believed that the ingredients, their preparation, and their use and the advantages thereof will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

I claim:

1. An ointment for the topical treatment of epidermal traumas selected from a group consisting of wounds, burns, lesions, rashes, and decubiti ulcers comprising a mixture of polymyxin, bacitracin, neomycin, iodine and sugar in an ointment base.

2. An ointment as described in claim 1 wherein: said polymyxin is in the form of polymyxin B sulfate.

3. An ointment as described in claim 1 wherein: said bacitracin is in the form of bacitracin zinc.

4. An ointment as described in claim 1 wherein: said neomycin is in the form of neomycin sulfate.

5. An ointment as described in claim 1 wherein: said iodine is in the form of povidone-iodine.

6. A method for treating epidermal traumas selected from a group consisting of wounds, burns, lesions, rashes, and decubital ulcers which comprises applying to the said epidermal traumas an effective amount of the ointment described in claim 1.

7. A method as described in claim 6 wherein: said application to said epidermal traumas is daily until healing occurs.

8. A method as described in claim 6 wherein: said epidermal traumas are decubital ulcers (bed sores).

9. A method as described in claim 6 wherein: said epidermal traumas are burns.

10. A method as described in claim 6 wherein: said epidermal traumas are wounds.

11. A method as described in claim 6 wherein: said epidermal traumas are lesions.

12. A method as described in claim 6 wherein: said epidermal traumas are rashes.

13. An ointment for the topical treatment of epidermal traumas as set forth in claim 1 wherein said mixture is in essentially the ratio of from 250 to 750 mg of sugar to from 5 to 15 mg of iodine to from 1 to 10 mg of neomycin to from 1,000 to 10,000 units of polymyxin to from 50 to 500 units of bacitracin in an said ointment base.

14. A method for treating epidermal traumas selected from a group consisting of wounds, burns, lesions, rashes, and decubital ulcers which comprises applying to the said epidermal traumas an effective amount of the ointment described in claim 13.

15. An ointment for the topical treatment of epidermal traumas as set forth in claim 13 wherein:
said neomycin is neomycin sulfate and said polymyxin is polymyxin B sulfate and said bacitracin is bacitracin zinc.

16. A method for treating epidermal traumas selected from a group consisting of wounds, burns, lesions, rashes, and decubital ulcers which comprises applying to the said epidermal traumas an effective amount of the ointment described in claim 15.

17. An ointment for the topical treatment of epidermal traumas as set forth in claim 15 wherein:
said iodine is providone-iodine (polyvinylpyrrolidone iodine).

18. A method for treating epidermal traumas selected from a group consisting of wounds, burns, lesions, rashes, and decubital ulcers which comprises applying to the said epidermal traumas an effective amount of the ointment described in claim 17.

19. An ointment for the topical treatment of epidermal traumas as set forth in claim 17 wherein:
said mixture is essentially in the ratio of 500 mg of said sugar to 90 mg of said providone to 10 mg of said iodine to 5 mg of said neomycin sulfate to 400 units of said bacitracin zinc to 5,000 units of said polymyxin B sulfate in about 394 mg of said ointment base.

20. A method for treating epidermal traumas selected from a group consisting of wounds, burns, lesions, rashes, and decubital ulcers which comprises applying to the said epidermal traumas an effective amount of the ointment described in claim 19.

* * * * *